United States Patent [19]

Inoue et al.

[11] Patent Number: 4,765,924

[45] Date of Patent: Aug. 23, 1988

[54] HALOGEN-CONTAINING HETEROCYCLIC COMPOUND AND LIQUID CRYSTAL COMPOSITION

[75] Inventors: Hiromichi Inoue; Takashi Inukai; Kouji Ohno; Kazutoshi Miyazawa; Shinichi Saito, all of Kanagawa, Japan

[73] Assignee: Chisso Corporation, Tokyo, Japan

[21] Appl. No.: 3,282

[22] Filed: Jan. 14, 1987

[30] Foreign Application Priority Data

Jan. 21, 1986 [JP] Japan ................... 61-10578

[51] Int. Cl.$^4$ .................. G02F 1/13; C09K 19/34; C07D 239/02; C07D 211/70
[52] U.S. Cl. ................ 252/299.61; 252/299.5; 252/299.01; 350/350 R; 350/350 S; 544/335; 546/339; 546/346
[58] Field of Search ........... 252/299.61, 299.5, 299.01; 350/350 R, 350 S; 544/335; 546/339, 346

[56] References Cited

U.S. PATENT DOCUMENTS

| 4,684,220 | 8/1987 | Shionozaki et al. | 252/299.61 |
| 4,684,477 | 8/1987 | Sugimori et al. | 252/299.61 |

FOREIGN PATENT DOCUMENTS

| 84194 | 7/1983 | European Pat. Off. | 252/299.61 |
| 194153 | 9/1986 | European Pat. Off. | 252/299.61 |
| 3315295 | 10/1984 | Fed. Rep. of Germany | 252/299.61 |
| 3515373 | 11/1986 | Fed. Rep. of Germany | 252/299.61 |
| 6124571 | 2/1986 | Japan | 252/299.61 |
| 8600087 | 1/1986 | World Int. Prop. O. | 252/299.61 |
| 2161808 | 1/1986 | United Kingdom | 252/299.61 |

OTHER PUBLICATIONS

Gray, G. W., et al., Liquid Crystals & Plastic Crystals, vol. 1, John Wiley & Sons, In., pp. 142–143 (1974).

Primary Examiner—Teddy S. Gron
Attorney, Agent, or Firm—Wenderoth, Lind & Ponack

[57] ABSTRACT

A novel liquid crystalline, halogen-containing heterocyclic compound having a characteristic that even when its $S_c^*$ phase is supercooled, no other smectic phases appear, and a liquid crystal composition containing the same are provided, which compound is expressed by the formula

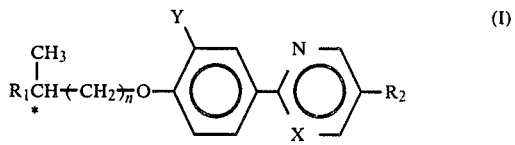

(I)

wherein $R_1$ and $R_2$ each represent an alkyl group of 2 to 18 carbon atoms; X represents $-N=$ or $-CH=$; Y represents F or Cl; n represents an integer of 0 to 10; and a symbol * represents an asymmetric carbon atom.

8 Claims, No Drawings

HALOGEN-CONTAINING HETEROCYCLIC COMPOUND AND LIQUID CRYSTAL COMPOSITION

BACKGROUND OF THE INVENTION

1. Field of the Invention

This invention relates to a novel liquid crystalline substance and a liquid crystal composition containing the same. More particularly it relates to a liquid crystalline substance containing an optically active group and a racemate thereof and further a chiral liquid crystal composition containing these.

The liquid crystalline substance referred to in the present invention includes not only compounds the liquid crystalline state of which can be observed by themselves, but also substances the liquid crystalline state of which cannot be observed by themselves, but which nevertheless have a chemical structure similar to that of the former compounds and are useful as a component constituting liquid crystal compositions.

2. Description of the Related Art

Twisted nematic (TN) type display mode has currently been most widely employed as liquid crystal display elements, but it is inferior in the response rate as compared with emissive type display elements such as electroluminescence, plasma display, etc., and various attempts for overcoming this drawback have been made, but, nevertheless, it seems that a possibility of improvement to a large extent has not been achieved. Thus, various liquid crystal display equipments based on different principles in place of TN type display elements have been attempted, and as one of them, there is a display mode utilizing ferroelectric liquid crystals (N. A. Clark and S. T. Layerwall, Applied Phys. Lett., 36,899 (1980)). This mode utilizes the chiral smectic C phase (hereinafter abbreviated to SC* phase) or chiral smectic H phase (hereinafter abbreviated to SH-phase) of ferroelectric liquid crystals, and these phases are preferred to be in the vicinity of room temperature. The present inventors have made various searches for liquid crystal substances containing an optically active group, mainly in order to develop liquid crystal substances suitable for being used for the above display mode, and as a result have attained the present invention.

SUMMARY OF THE INVENTION

The present inventors have searched for various liquid crystal substances having an optically active group mainly in order to develop liquid crystal substances suitable to be utilized for the abovementioned mode and have achieved the present invention.

The present invention resides in a liquid crystalline, optically active, halogen-containing heterocyclic compound expressed by the formula

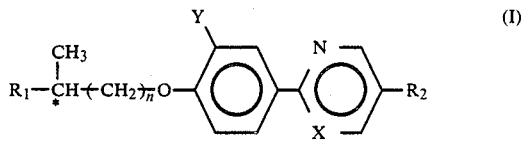

(I)

wherein $R_1$ and $R_2$ each represent an alkyl group of 2 to 18 carbon atoms; X represents $-N=$ or $-CH=$; Y represents F or Cl; n represents an integer of 0 to 10; and the symbol * represents an asymmetric carbon atom, and its racemates and further a chiral smectic liquid crystal composition containing at least one memeber thereof.

DETAILED DESCRIPTION OF PREFERRED EMBODIMENTS

Compounds of the formula (I) wherein X is $-N=$ i.e. expressed by the formula

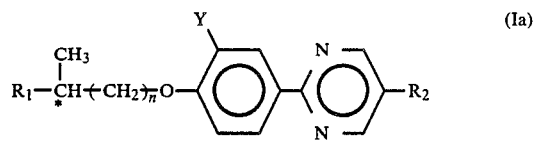

(Ia)

wherein $R_1$, $R_2$, Y, n and * are as defined above, are 2-aryl-substituted-5-alkylpyrimidines.

Compounds of the formula (I) wherein X is $-CH=$ i.e. expressed by the formula

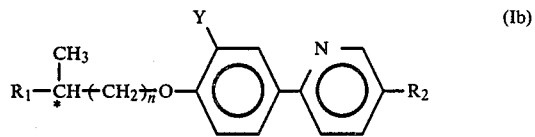

(Ib)

wherein $R_1$, $R_2$, Y, n and * are as defined above, are 2-aryl-substituted-5-alkylpyridines.

The phase transition points of representative examples of the compounds expressed by the formula (Ia) and those expressed by the formula (Ib) are shown in Table 1 and Table 2.

TABLE 1

| Sample No. | In formula (I) $R_1$ | $R_2$ | Y | n | Stereo-chemical configuration | Phase transition point (°C.) C | $S_c$* | $S_A$ | Ch | I |
|---|---|---|---|---|---|---|---|---|---|---|
| a1 | $C_2H_5$ | $C_2H_5$ | F | 2 | S | . 17.8 | — | — | — | . |
| a2 | $C_2H_5$ | $C_8H_{17}$ | F | 2 | S | . 39.2 | — | — | — | . |
| a3 | $C_2H_5$ | $C_9H_{19}$ | F | 2 | S | . 42.2 | — | — | — | . |
| a4 | $C_2H_5$ | $C_{12}H_{25}$ | F | 1 | S | . 39.2 | — | (. 37.3) | — | . |
| a5 | $C_2H_5$ | $C_{12}H_{25}$ | F | 2 | S | . 37.5 | — | (. 36.4) | — | . |
| a6 | $C_2H_5$ | $C_6H_{13}$ | F | 3 | S | . 21.0 | (. 19.0) | . 27.0 | — | . |
| a7 | $C_2H_5$ | $C_7H_{15}$ | F | 3 | S | . 39.5 | (. 28.1) | . 41.7 | — | . |
| a8 | $C_2H_5$ | $C_8H_{17}$ | F | 3 | S | . 35.2 | . 36.9 | . 41.0 | — | . |
| a9 | $C_2H_5$ | $C_8H_{17}$ | F | 3 | racemic | . 36.5 | . 37.3 | . 41.8 | — | . |
| a10 | $C_2H_5$ | $C_9H_{19}$ | F | 3 | S | . 40.4 | . 44.4 | . 47.1 | — | . |
| a11 | $C_2H_5$ | $C_{12}H_{25}$ | F | 3 | S | . 37.9 | . 49.0 | . 49.2 | — | . |
| a12 | $C_2H_5$ | $C_7H_{15}$ | F | 4 | S | . 30.0 | — | . 38.7 | — | . |
| a13 | $C_2H_5$ | $C_8H_{17}$ | F | 4 | S | . 39.2 | (. 30.6) | (. 38.6) | — | . |
| a14 | $C_2H_5$ | $C_9H_{19}$ | F | 4 | S | . 36.0 | . 37.5 | . 44.5 | — | . |
| a15 | $C_2H_5$ | $C_{12}H_{25}$ | F | 4 | S | . 37.1 | . 47.3 | — | — | . |

TABLE 1-continued

| Sample No. | In formula (I) R$_1$ | R$_2$ | Y | n | Stereo-chemical configuration | Phase transition point (°C.) C | S$_c$* | S$_A$ | Ch | I |
|---|---|---|---|---|---|---|---|---|---|---|
| a16 | C$_2$H$_5$ | C$_3$H$_7$ | F | 5 | S | . 46.0 | — | — | — | . |
| a17 | C$_2$H$_5$ | C$_4$H$_9$ | F | 5 | S | . 27.4 | — | — | — | . |
| a18 | C$_2$H$_5$ | C$_5$H$_{11}$ | F | 5 | S | . 59.0 | — | — | (. 25.7) | . |
| a19 | C$_2$H$_5$ | C$_6$H$_{13}$ | F | 5 | S | . 28.9 | (. 16.8) | (. 26.0) | (. 27.5) | . |
| a20 | C$_2$H$_5$ | C$_7$H$_{15}$ | F | 5 | S | . 29.2 | (. 23.0) | . 42.1 | — | . |
| a21 | C$_2$H$_5$ | C$_8$H$_{17}$ | F | 5 | S | . 10.0 | . 33.2 | . 43.0 | — | . |
| a22 | C$_2$H$_5$ | C$_9$H$_{19}$ | F | 5 | S | . 26.0 | . 42.3 | . 51.0 | — | . |
| a23 | C$_2$H$_5$ | C$_{12}$H$_{25}$ | F | 5 | S | . 46.0 | . 53.1 | — | — | . |
| a24 | C$_2$H$_5$ | C$_8$H$_{17}$ | F | 6 | S | . 2.0 | . 24.3 | . 42.3 | — | . |
| a25 | C$_2$H$_5$ | C$_2$H$_5$ | F | 7 | S | . 27.4 | — | — | — | . |
| a26 | C$_2$H$_5$ | C$_8$H$_{17}$ | F | 7 | S | . 16.0 | . 34.8 | . 45.2 | — | . |
| a27 | C$_6$H$_{13}$ | C$_8$H$_{17}$ | F | 0 | S | . 0.0 | — | — | — | . |
| a28 | C$_8$H$_{17}$ | C$_8$H$_{17}$ | F | 1 | S | . 31.0 | — | — | — | . |
| a29 | C$_2$H$_5$ | C$_8$H$_{17}$ | Cl | 5 | S | . 37.8 | — | — | — | . |

TABLE 2

| Sample No. | In formula (I) R$_1$ | R$_2$ | Y | n | Stereo-chemical configuration | Phase transition point (°C.) C | S$_c$* | S$_A$ | I |
|---|---|---|---|---|---|---|---|---|---|
| b1 | C$_2$H$_5$ | C$_6$H$_{13}$ | F | 4 | S | . 16.5 | . 21.5 | . 26.3 | . |
| b2 | C$_2$H$_5$ | C$_6$H$_{13}$ | F | 5 | S | . 7.0 | . 30.8 | . 32.8 | . |
| b3 | C$_2$H$_5$ | C$_7$H$_{15}$ | F | 3 | S | . 21.0 | . 35.1 | . 40.4 | . |
| b4 | C$_2$H$_5$ | C$_8$H$_{17}$ | F | 3 | S | . 37.3 | . 39.8 | . 42.1 | . |
| b5 | C$_2$H$_5$ | C$_8$H$_{17}$ | F | 4 | S | . 33.0 | . 33.5 | . 39.4 | . |
| b6 | C$_2$H$_5$ | C$_9$H$_{19}$ | F | 4 | S | . 22.7 | . 51.0 | . 54.5 | . |
| b7 | C$_2$H$_5$ | C$_{10}$H$_{21}$ | F | 1 | S | . 24.0 | — | . 32.3 | . |
| b8 | C$_2$H$_5$ | C$_{10}$H$_{21}$ | F | 3 | S | . 38.0 | . 42.8 | . 45.4 | . |
| b9 | C$_6$H$_{13}$ | C$_7$H$_{15}$ | F | 0 | R | liquid at room temperature | | | . |
| b10 | C$_2$H$_5$ | C$_4$H$_{17}$ | F | 5 | S | . 21.5 | . 43.2 | . 45.8 | . |
| b11 | C$_2$H$_5$ | C$_9$H$_{19}$ | F | 7 | S | . 24.0 | . 50.0 | . 54.0 | . |

As seen from Table 1 and Table 2, most of the optically active substances among the compounds of the formula (I) of the present invention exhibit S$_c$* phase at relatively low temperatures and within a broad temperature range in the vicinity of room temperature; hence they are very useful compounds for constituting liquid crystal compositions suitable to be used for light-switching mode utilizing ferroelectric properties. Further, the racemates among the compounds of the formula (I) exhibit S$_c$ phase in place of S$_c$* phase, but their phase transition points are almost the same as those of the corresponding optically active substances, and if necessary by blending the racemates with the optically active substances, it is possible to utilize them for adjusting the helical pitch or cholesteric pitch of S$_c$* phase or for other purposes.

Further, the compounds of the formula (I) have a superior compatibility with other compounds exhibiting S$_c$* phase or S$_H$* phase, compounds exhibiting cholesteric phase, etc.; hence admixture of the compounds of the formula (I) with such other compounds is very effective for extending the temperature range in which S$_c$* phase is exhibited, particularly the lower temperature range.

Another specific feature of the compounds of the present invention consists in that the halogen atom is present as a substituent on the lateral side. It is at present very difficult to anticipate in what manner the change of the phase transition points due to replacement of hydrogen atom of the unsubstituted compound by the halogen atom or the like achieves in specified liquid crystal compounds. In general, there is a tendency that the upper limit temperature of liquid crystal phases, i.e., the clearing point thereof is reduced, but the extent of the reduction cannot be anticipated so that it is unclarified until a specified compound is practically prepared and its properties are measured. This applies even to the case of relatively simple liquid crystal phases such as nematic phase, and it applies much more to the case of smectic liquid crystals mainly aimed at in the present invention since various smectic modification are present in that case.

Noting such point, the present inventors have made research on compounds containing a halogen atom on the lateral side thereof and as a result have achieved the present invention. Hereinafter, concretely, comparative data relative to the case where a halogen atom is introduced on the lateral side and the case where no halogen atom is introduced thereon will be illustrated and also the effectiveness will be mentioned. (a) Case of pyrimidine compounds of the formula (Ia):

The comparisons of the phase transition points of compounds of the formula (Ia) of the present invention with those of the corresponding compounds having no substituent (X corresponds to hydrogen atom H) are exemplified in Table 3.

TABLE 3

| Sample No. | Phase transition points (°C.) C | S$_x$ | S$_c$* | S$_A$ | Ch | I |
|---|---|---|---|---|---|---|
| a8 | . 35.2 | — | . 36.9 | . 41.0 | — | . |
| unfluorinated*[1] | . 31.2 | (. 16.8/S$_B$) | . 46.8 | . 50.8 | — | . |
| a10 | . 40.4 | — | . 44.4 | . 47.1 | — | . |
| unfluorinated*[1] | . 23.0 | . 28.0 | . 30.0 | . 51.5 | . 52.0 | . |
| a11 | . 37.9 | — | . 49.0 | . 49.2 | — | . |
| unfluorinated*[1] | . 41.0 | (. 23.8) | . 62.2 | — | — | . |
| a15 | . 37.1 | . | . 47.3 | — | — | . |
| unfluorinated*[1] | . 23 | (. 16) | . 61.5 | — | — | . |
| a21 | . 10.0 | — | . 33.2 | . 43.0 | — | . |
| unfluorinated* | . 3.0 | (. 14.2/S$_B$) | . 48.6 | . 56.3 | — | . |

*[1]Data from Japanese patent application laid-open No.Sho61-93170

As apparent from teh above comparative data, although the upper limit of temperature of S$_c$* phase is liable to lower to some extent by the incorporation of halogen atom as in the formula (Ia) compounds of the present invention, a surprising effectiveness is obtained that appearances of other undesirable smectic phases (more highly ordered smectic modifications) at lower temperatures are surpressed. Actually, in the case of compounds of sample No. a21, no other smectic phases appear even if they are supercooled down to −13° C., for example. At this point they are crystallized and the behavior at a lower temperature than −13° C. could not be observed. (b) Case of pyridine compounds (1b):

Examples in comparison of the phase transition points of compounds of the present invention in Table 2 with those of compounds having no F substituent on the lateral side i.e. compounds of Y=H in the formula are shown in Table 4.

TABLE 4

| Sample No. | Phase transition points (°C.) | | | | | | |
|---|---|---|---|---|---|---|---|
| | C | $S_H*$ | $S_G*$ | $S_F*$ | $S_c*$ | $S_A$ | I |
| b2 | . 7.0 | — | — | — | . 30.8 | . 32.8 | . |
| Unfluorinated | . 45.2 | (. 44.2) | . 48.5 | . 53.8 | . 63.0 | — | . |
| b4 | . 37.3 | — | — | — | . 39.8 | . 42.1 | . |
| Unfluorinated | . 30.5 | — | . 34.8 | . 51.0 | . 62.7 | — | . |
| b5 | . 33.0 | — | — | — | . 33.5 | . 39.4 | . |
| Unfluorinated | . 21.5 | — | (. 9.7) | . 38.5 | . 59.1 | — | . |
| b6 | . 22.7 | — | — | — | . 51.0 | . 54.5 | . |
| Unfluorinated | . 33.5 | — | — | . 45.4 | . 63.0 | — | . |
| b8 | . 38.0 | — | — | — | . 42.8 | 45.4 | . |
| Unfluorinated | . 35.5 | — | — | . 53.0 | . 64.0 | — | . |

The of unfluorinated compounds listed in Table 4 for comparison are disclosed in the prior patent application previously filed by the present inventors (Japanese patent application No. Sho 60-293934/1985), and in any case of the compounds, $S_F*$ phase, $S_G*$ phase, etc. appear at temperatures lower than those of $S_G*$ phase, whereas in the case of compounds of the formula (Ib) of the present invention, $S_c*$ phase remains as it is, down to −15° C. in a supercooled state and other smectic phases as above are not observed. Thus it can been seen that introduction of a halogen atom on the lateral side has an effectiveness of notably inhibiting the appearance of smectic phases other than $S_c*$ phase at temperatures lower than that of $S_c*$ phase.

Here, the difference between the prior art particularly related to compounds of the formula (Ia) among those of the present invention, that is, Japanese patent application laid-open No. Sho 59-210070/1984 (DE Patent No. 3315295.0) and the present invention will be described.

In the prior art, Japanese patent application laidopen No. Sho 59-210070/1984, a large number of arylpyridines having a fluorine substituent in the aryl group are claimed. In the prior art, compounds of 90 general formulas are disclosed and about 196 compounds are enumerated. However, compounds the phase transition points of which are concretely shown are only the following 5 compounds:

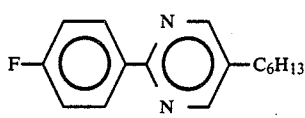 mp 39° C.

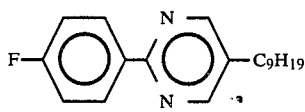 mp 23.5° C.

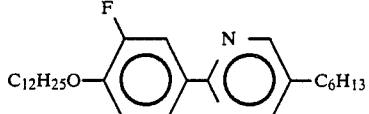 mp 51.5° C., Cl.p. 44° C.

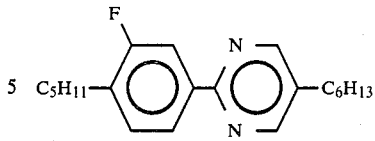 mp 30° C.

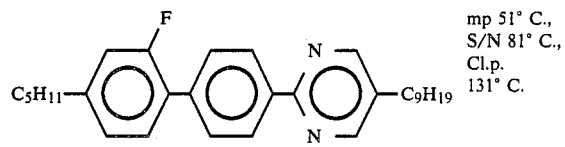 mp 51° C., S/N 81° C., Cl.p. 131° C.

The prior art describes that these compounds have a superior specific feature that addition thereof to other liquid crystals notably inhibits a smectic phaseforming tendency which is undesirable for liquid crystal compositions for display elements using nematic phase.

The compounds of the formula (Ia) of the present invention may be possibly included in the claimed compounds in the prior art in a broad sense, but the compounds of the formula (Ia) themselves exhibit smectic phase. A compound most related to the compounds of the formula (Ia) among the above-mentioned five compounds is, of course,

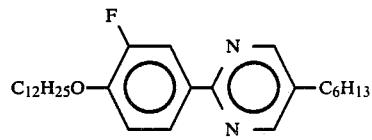

However, this compound has a linear chain alkoxy group unlike the compounds of the formula (Ia) of the present invention, and according to the description of the prior art, it exhibits only a nematic phase; hence it has nothing to do with the chiral smectic compounds mainly aimed at in the present invention. In addition, the prior art discloses in an extremely general expression that the alkyl group may be a branched chain, optically active group, but no compounds having a branched chain alkyl group are found even among the above-mentioned 196 compounds, not to mention Examples.

When chiral smectic liquid crystal compositions are composed using the compounds of the formula (I), it is possible to form them from a plurality of compounds of the formula (I), alone, and it is also possible to prepare liquid crystalline compositions exhibiting $S_c*$ phase, by mixing compounds of the formula (I) with other smectic liquid crystals.

When the light switching effect of the $S_c*$ phase is applied to display elements, the resulting display elements have the following three superior specific features:

The first specific feature is that the elements reply at a very high rate and the response times are 1/100 or less of those of display elements according to the usual TN display mode.

The second specific feature is that the elements have a memory effect; hence multiplex drive is easy in combination of this effect with the above-mentioned high rate response properties.

The third specific feature is that gray scale in TN display mode is attained by controlling the impressed voltage applied to display elements, but this is accompanied with difficult problems of the temperature dependency of threshold voltage value and the voltage dependency of response rate. However, in the case where the light switching effect of $S_c^*$ phase is applied to the display elements, it is possible to easily attain the gray scale by controlling the switching time of polarity; hence the display elements are very suitable for graphic display.

As for the display modes, the following two modes may be considered:

one mode is of birefringence type using two pieces of polarizers and another is of guest-host type using dichroic dyestuffs. Since $S_c^*$ phase has a spontaneous polarization, molecules reverse around the helical axis thereof as a revolving axis by reversing the polarity of impressed voltage. A liquid crystal composition having $S_c^*$ phase is filled into a liquid crystal display cell subjected to an aligning treatment so that liquid crystal molecules can align in parallel to the surface of electrodes, followed by placing the liquid crystal cell between two pieces of polarizers arranged so that the director of the liquid crystal molecules can be in parallel to the polarization plane on another side, impressing a voltage and reversing the polarity to be thereby able to obtain a bright field and a dark field (determined by the opposed angles of polarizers). On the other hand, in the case where display elements are operated in guest-host mode, it is possible to obtain bright field and colored field (determined by the arrangement of polarization sheets) by reversing the polarity of impressed voltage. In general, it is difficult to align liquid crystal molecules in smectic state in parallel to the wall surface of glass; hence liquid crystal molecules have been aligned by cooling them very slowly (e.g. 1°~2° C./hr) initially starting from their isotropic liquid, in a magnetic field of several tens Kilogauss or more, but in the case of liquid crystal substances having cholesteric phase, the substances are cooled at a cooling rate of 1° C./min. under impression of a direct current voltage of 50 to 100V in place of magnetic field, whereby it is possible to easily obtain a monodomain state where liquid crystal molecules are uniformly aligned.

Compounds of the formula (I) also have an optically active carbon atom; hence when they are added to nematic liquid crystals, they have a performance of having a twisted structure induced in the mixtures. Nematic liquid crystals having a twisted structure, i.e. chiral nematic liquid crystals, do not form the so-called reverse domain of TN type display elements; hence it is possible to use the compounds of the formula (I) as an agent for preventing the reverse domain.

Next, preparation of the compounds of the formula (I) of the present invention will be described. Firstly, compounds of the formula (I) wherein X represents —N═, i.e. compounds of the formula (Ia), may be most suitably prepared through the following passageway 1 or 2: (Passageway 1)

(Passageway 1)

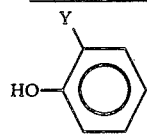

(a)

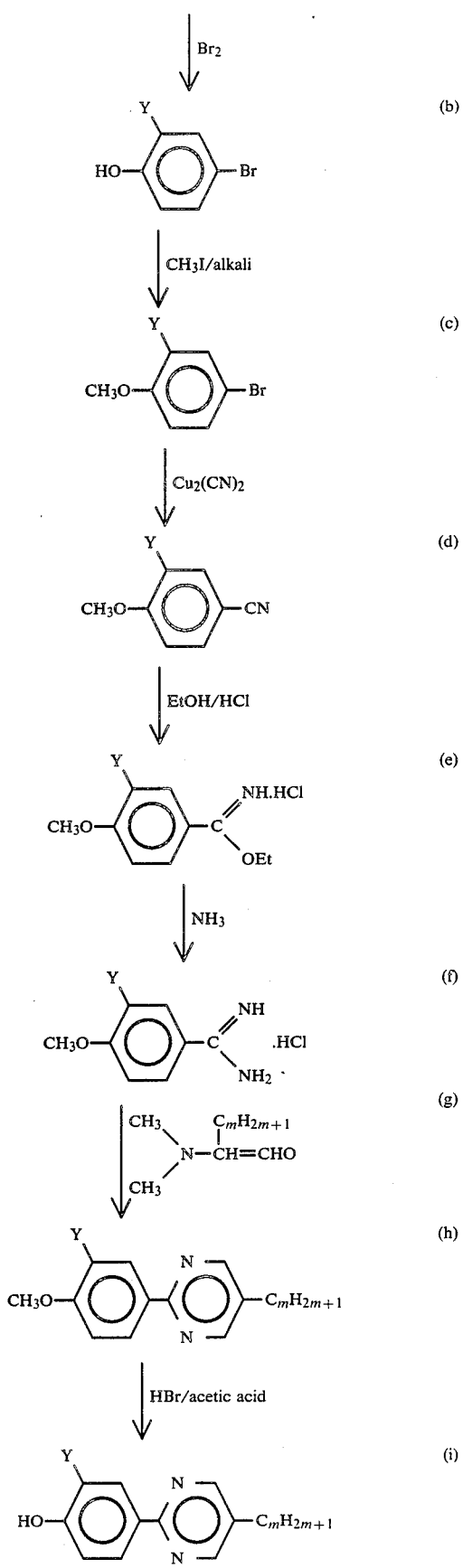

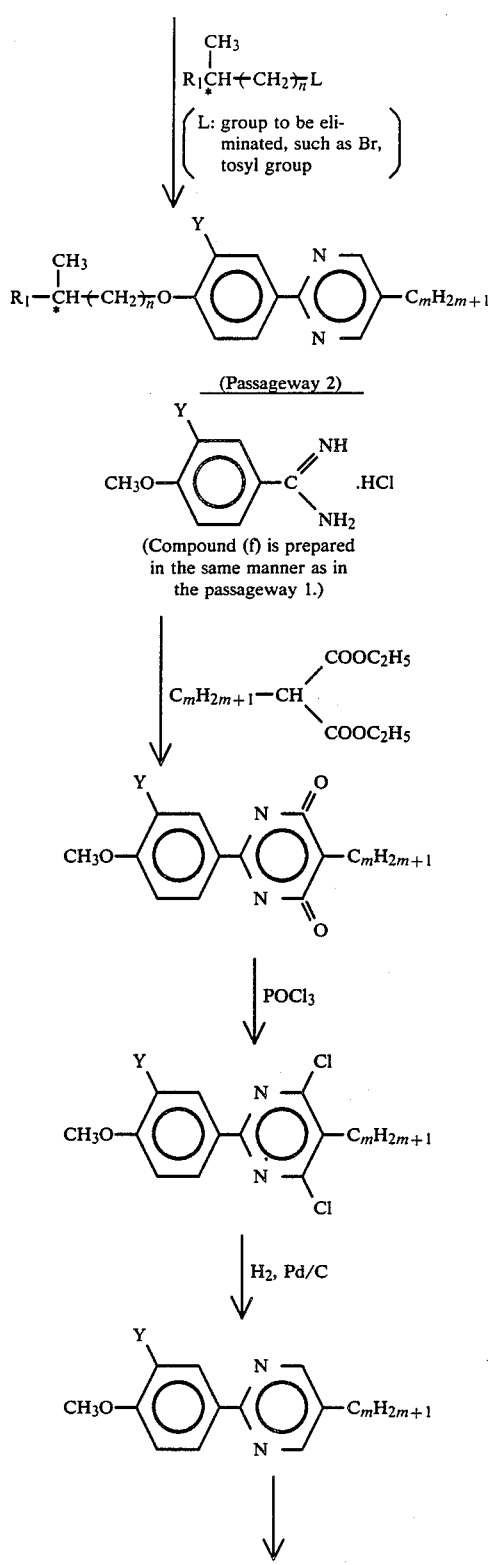

(Passageway 2)

(Compound (f) is prepared in the same manner as in the passageway 1.)

The succeeding steps are the same as those in the passageway 1.

In the case of compounds of m=9 or more, in the above pasageways, passageway 2 is commercially more suitable than passageway 1, because N,N-dimethylaminoalkylacroleins (g) of m=9 or more used in the passageway 1 are not suitable to mass production.

Next, compounds of the formula (I) wherein X is —CH= i.e. compounds of the formula (Ib) may be most suitably prepared through the following preparation passageway:

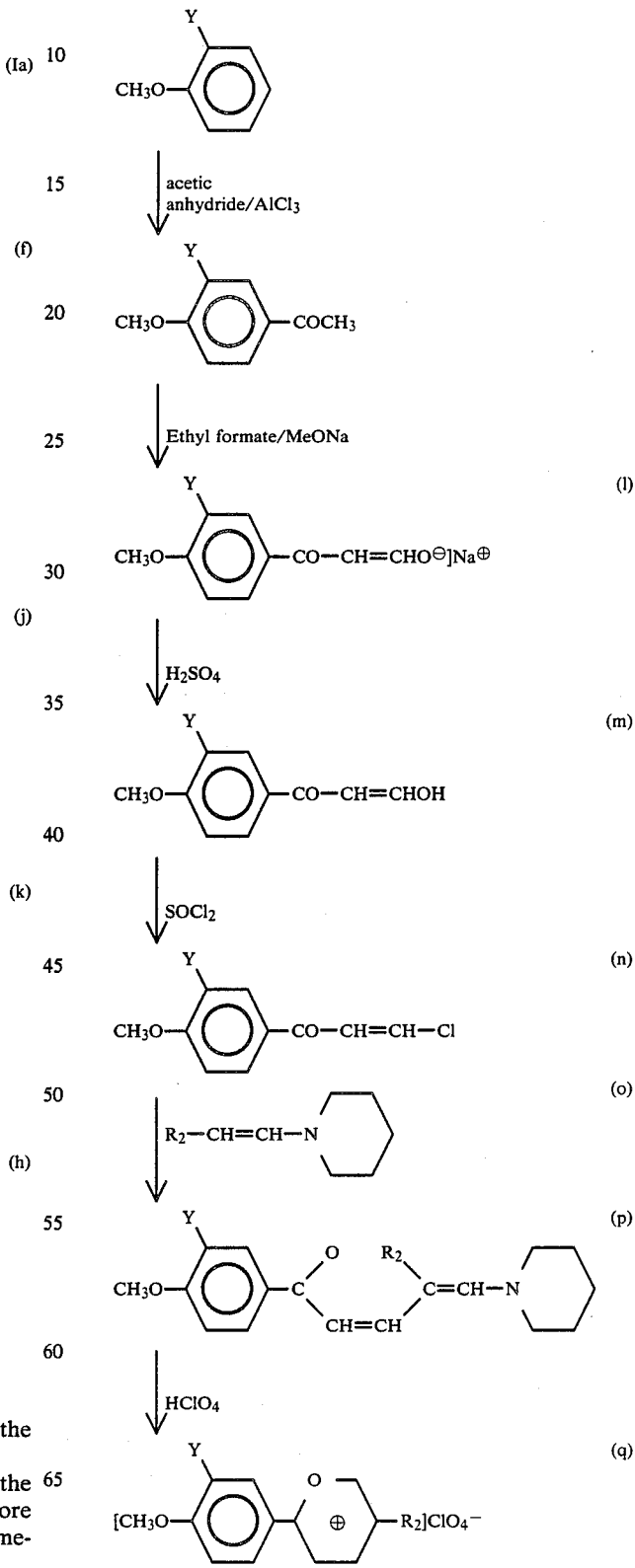

-continued

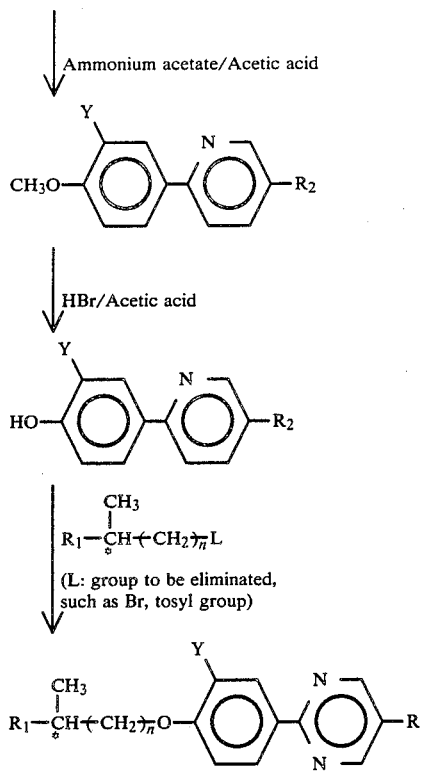

In addition, in either of (Ia) or (Ib), when an optically active compound is used as

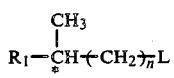

to be reacted at the final step, the final product is also optically active, while when a racemate is used, the final product is racemic.

The compounds and liquid crystal composition of the present invention will be described in more detail by way of Examples.

EXAMPLE 1

Preparation of (S)-2(p-6-methyl-octyloxy-m-fluorophenyl)-5-octyl-pyrimidine (a compound of the formula (Ia) wherein $R_1=C_2H_5$, $R_2=n-C_8H_{17}$, $X=-N=$, $Y=F$ and $n=5$; sample No. a21)

(i) Preparation of 2-(p-hydroxy-m-fluorophenyl)-5-octylpyrimidine ((i); Y=F).

o-Fluoro-p-cyanoanisole as a known substance (m.p. 98.5°–99.5° C., (d); Y=F) was reacted with anhydrous ethanol and hydrogen chloride in toluene to obtain an iminoether hydrogen chloride salt ((e); Y=F), which was then reacted with ammonia gas without its isolation, followed by removing ammonium chloride by filtration and thereafter distilling off the solvent to obtain an amidine hydrogen chloride salt ((f); Y=F), which was heated without particular purification, with an equivalent quantity of N,N-dimethylamino-octyl-acrolein ((g); m=8) in the presence of an alkali to obtain 2-(p-methoxy-m-fluorophenyl)-5-octyl-pyrimidine ((h); Y=F, m=8, m.p. 58.7°–59.0° C.). The above-mentioned process is a known chemical method in the case of an unsubstituted compound where of Y=H.

This 2-(p-methoxy-m-fluorophenyl)-5-octylpyrimidine (50 g) was heated for substitution together with glacial acetic acid (500 ml) and hydrobromic acid (47%) (170 g) for 72 hours, followed by distilling off acetic acid and hydrobromic acid under reduced pressure, adding aqueous NaOH and toluene, extracting the objective substance into the toluene layer and then distilling off toluene to obtain 2-(p-hydroxy-m-fluorophenyl)-5-octylpyrimidine ((i); Y=F, m=8) (48.5 g). This product was used in the next stage without its purification.

(ii) Preparation of the captioned compound

Compound (I) (Y=F, m=8) (5.0 g) obtained in the paragraph (i) was dissolved in an ethanol solution containing KOH (1.3 g), followed by adding (S)-6-methyloctyl-bromide (46 g), heating the mixture under reflux for 5 hours, distilling off ethanol under reduced pressure, extracting the resulting product with ether, washing the ether layer with water, distilling off ether and recrystallizing the residue from ethanol to obtain the objective captioned compound (3.4 g). This product had the following phase transition points:

$C-S_c^*$ point: 10.0° C., $S_c^*-S_A$ point: 33.2° C., and $S_A-I$ point: 43.0° C. Further, the $S_c^*$ phase was cooled to examine whether another smectic phase is present or not. As a result, supercooling down to $-13°$ C. was possible while $S_c^*$ phase was kept as it was, and the product crystallized without any appearance of another smectic phase.

Further, the elemental analysis values thereof accorded well with its calculated values as follows:

|   | Analytical values (%) | Calculated values (in terms of $C_{27}H_{41}FN_2O$) |
|---|---|---|
| C | 75.6 | 75.65 |
| H | 9.8 | 9.44 |
| N | 6.5 | 6.54 |
| F | 4.4 | 4.43 |

In the same manner as the above, it is possible to prepare other compounds of the formula (Ia) wherein the carbon number of $R_2$ is 8 or less. Representative examples of such other compounds are shown in Table 1.

In addition, in the above second stage (ii), it is possible to use a branched alkyl tosylate in place of the branched alkyl bromide. However, in the preparation of compounds which are optically active and wherein n=0, it is preferred to use a branched alkyl tosylate, not the branched alkyl bromide. The reason is that when an optically active alkyl bromide,

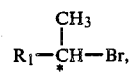

is prepared from the corresponding optically active, secondary alcohol,

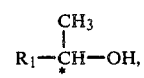

reduction in the optical purity is difficultly avoidable. Whereas, in the case of preparation of an optically active tosylate, no reduction in the optical purity occurs.

EXAMPLE 2

Preparation of (S)-2(p-5-methyl-heptyloxy-m-fluorophenyl)-5-nonyl-pyrimidine (a compound of the formula (Ia) wherein $R_1=C_2H_5$, $R_2=n-C_9H_{19}$, $Y=F$ and $n=4$; sample No. a14)

p-Methoxy-m-fluorobenzamidine hydrogen chloride salt ((f); $Y=F$) (40.9 g, 0.2 mol) and n-nonyl diethylmalonate (b.p. 153°/5 mmHg) (57.3 g, 0.2 mol) were heated under reflux with stirring in the presence of sodium ethoxide (0.66 mol) dissolved in ethanol (550 ml) for 6 hours, followed by acidifying the resulting material with dilute hydrochloric acid to obtain light yellow solids (64 g, m.p. 271°–274° C.) ((j); $Y=F$, $m=9$).

This substance (64 g) was heated under reflux together with phosphorus oxychloride ($POCl_3$) (385 ml) in the presence of N,N-diethylaniline (40 ml) for 19 hours, followed by distilling off excess $POCl_3$, pouring the residue into ice and recrystallizing the resulting solids from pentane to obtain 2-(p-methoxy-m-fluorophenyl)-4,6-dichloro-5-nonyl-pyrimidine ((k); $Y=F$, $m=9$) (m.p. 59°–60° C.) (35.8 g).

This dichloro compound (35.7 g) was hydrogenated under the atmospheric pressure in the presence of Pd on carbon catalyst in the presence of triethylamine (34 g) in ethanol, followed by recrystallizing the resulting product from ethanol to obtain (S)-2-(p-methoxy-m-fluorophenyl)-5-nonyl-pyrimidine ((h); $Y=F$, $m=9$) (m.p. 55°–56° C.) (23.4 g).

This product was demethylated with hydrobromic acid/glacial acetic acid in the same manner as in Example 1, to obtain 2-(p-hydroxy-m-fluorophenyl)-5-nonyl-pyrimidine ((i); $Y=F$, $m=9$) (m.p. 46°–47.5° C.) (recrystallized from n-heptane).

Etherification of the above compound of (i) ($Y=F$, $m=9$) with (S)-5-methyl-heptyl bromide was carried out in the same manner as in the step (ii) of Example 1. The resulting captioned compound had the following phase transition points:
C-$S_c^*$: 36° C., $S_c^*$-SA 37.5° C., SA-I: 44.5° C.

In the same manner as the above, it is possible to prepare any of the other compounds of the formula (Ia) wherein $R_2=n-C_9H_{19}$ or longer chain.

EXAMPLE 3

Preparation of (S)-2-(p-5-methyl-heptyloxy-m-fluorophenyl)-5-octyl-pyridine (a compound of the formula (Ib) wherein $R_1=C_2H_5$, $R_2=n-C_8H_{17}$, $Y=F$, and $n=4$; sample No. b5)

Sodium methoxide (10.6 g, 0.196 mol) and toluene (600 ml) were agitated at room temperature, followed by dropwise adding to the mixture, a solution of m-fluoro-p-methoxyacetophenone as a known compound (30 g, 0.178 mol), ethyl formate (13.2 g, 0.178 mol) and toluene (200 ml), keeping the mixture at room temperature for 8 hours with stirring, adding water (500 ml), transferring the resulting mixture into a separating funnel (the material corresponding to an aqueous solution of compound ((l); $Y=F$), adding to the aqueous solution, an aqueous solution of conc. sulfuric acid (6 ml) and water (180 ml), dissolving deposited crystals ((m); $Y=F$) in fresh toluene, drying the toluene solution of the compound (m) with calcium chloride, slowly dropwise adding thionyl chloride (40 ml) under cooling, heating the mixture under reflux for one hour, distilling off the solvent and excess thionyl chloride under reduced pressure, and recrystallizing the residue from heptane to obtain m-fluoro-p-methoxyphenyl-$\beta$-chlorovinyl ketone ((n); $Y=F$) (18.5 g).

N-decenylpiperidine ((o); $R_2=C_8H_{17}$) (b.p. 117°–118° C. (2.5 mmHg)) (20.8 g, 0.093 mol) and triethylamine (9.4 g, 0.093 mol) were dissolved in ethyl ether (100 ml) with stirring, followed by dropwise adding to the solution, a solution of m-fluoro-p-methoxyphenyl-$\beta$-chlorovinyl ketone (18.5 g, 0.093 mol) obtained above and ethyl ether (250 ml), agitating the mixture at room temperature for 8 hours, adding water (50 ml) and toluene (30 ml), transferring the mixture into a separating funnel, twice washing the organic layer with water, distilling off the solvent from the organic layer under reduced pressure, adding to the resulting residue ((p); $Y=F$, $R_2=C_8H_{17}$), perchloric acid (70%) (36 ml), thereafter adding water (36 ml), heating the mixture under reflux for 10 minutes, cooling, washing the resulting crystals with ethyl ether, and drying the crystals to obtain 2-(m-fluoro-p-methoxyphenyl)-5-octyl-pyrilium perchlorate ((q); $Y=F$, $R_2=C_8H_{17}$) (21.3 g). N-decenylpiperidine as its raw material was prepared from n-caprinaldehyde and piperidine according to the method of Mannich et al (Chem. Ber. 69, 2106 (1936)).

This 2-(m-fluoro-p-methoxyphenyl)-5-octylpyrilium perchlorate (21.3 g, 0.051 mol) was heated under reflux with stirring together with ammonium acetate (39.3 g, 0.510 mol) and acetic acid (500 ml) for 4 hours, followed by pouring the reaction fluid in water, dissolving the resulting crystals in toluene, transferring the solution into a separating funnel, three times washing it with water, distilling off the solvent under reduced pressure and recrystallizing the residue to obtain 2-(m-fluoro-p-methoxyphenyl)-5-octyl-pyridine ((r); $Y=F$, $R_2=C_8H_{17}$) (10.3 g). This product had a m.p. of 41.0°–48.3° C. To this 2-(m-fluoro-p-methoxyphenyl)-5-pyridine (10.3 g, 0.033 mol) were added hydrobromic acid (47%) (50 ml) and acetic acid (140 ml), followed by heating the mixture under reflux for 30 hours, cooling, pouring it in water, filtering off the resulting crystals, dissolving the crystals in 2N NaOH aqueous solution, adding acetic acid to make the solution acidic, filtering off crystals and recrystallizing to obtain 2-(m-fluoro-p-hydroxyphenyl)-5-octyl-pyridine ((s); $Y=F$, $R_2=C_8H_{17}$) (7 g). This product had a m.p. of 73.5°–74.6° C.

To this 2-(m-fluoro-p-hydroxyphenyl)-5-octylpyridine (2 g, 0.007 mol) were added ethanol (20 ml), KOH (0.4 g, 0.007 mol) and optically active 5-methylheptyl bromide (1.4 g, 0.007 mol), followed by heating the mixture under reflux with stirring for 4 hours, cooling, adding water and toluene, transferring the mixture into a separating funnel, washing the resulting organic layer with 2N-NaOH aqueous solution, washing with water, distilling off the solvent under reduced pressure and recrystallizing the residue in a freezer to obtain the objective optically active (S)-2-p-5-methyl-heptyloxy-m-fluorophenyl)-5-octylpyridine (1.8 g).

This product had the following phase transition points:

C-$S_c^*$: 33.0° C., $S_c^*$-SA: 33.5° C., SA-I: 39.4° C. Further, the elemental analysis values accorded well with its calculated values as follows:

|   | Observed values (%) | Calculated values (in terms of $C_{27}H_{40}FNO$) |
|---|---|---|
| C | 78.3 | 78.40 |
| H | 9.6 | 9.75 |
| F | 4.5 | 4.59 |
| N | 3.3 | 3.39 |

In the same manner as in this Example, it is possible to prepare any of the compounds of the formula (Ib) The values of physical properties of other representative examples are shown in Table 2.

EXAMPLE 5 (USE EXAMPLE 2)

Using a liquid crystal compound of the present invention (sample No. a21) and other optically active, chiral smectic liquid crystal compounds, a liquid crystal composition having the following components was prepared:

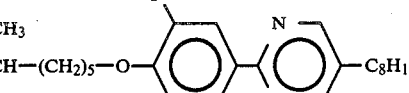

EXAMPLE 4 (USE EXAMPLE 1)

Using the liquid crystal compounds of the present invention, the following composition in equal weights:

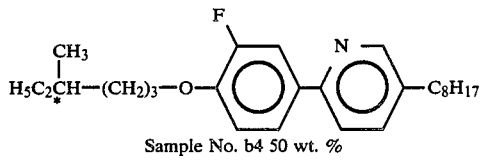

Sample No. b4 50 wt. %

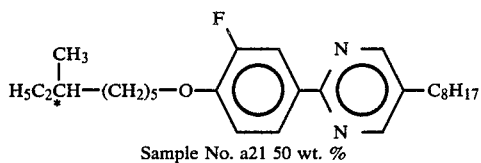

Sample No. a21 50 wt. %

The resulting composition was filled in a cell 2 μm thick, provided with transparent electrodes obtained by applying polyvinyl alcohol (PVA) as an agent for aligning treatment, followed by rubbing the resulting surface to subject it to parallel aligning treatment. The resulting liquid crystal element was provided between two sheets of crossed polarizers and an electric field was impressed. As a result, a change in the intensity of transmitted light was observed by impression of 20V.

From the change in the intensity of transmitted light at that time was sought the response time to give about 500 μsec at 25° C.

In addition, the above composition exhibits a m.p. of 5° C. and a $S_c^*$-SA transition point of 34° C. Its supercooled state is observed down to −45° C. and the composition has $S_c^*$ phase as far as this temperature and also no other smectic phase appears.

The resulting composition was filled in the same cell of 2 μm thick as in Example 4, and the resulting liquid crystal element was provided between two sheets of crossed polarizers and an electric field was impressed. As a result, a change in the intensity of transmitted light was observed by impression of 20V.

From the change in the intensity of transmitted light was sought the response time to give a value of about 200 μsec at 25° C.

The upper limit temperature of $S_c^*$ phase of the above liquid crystal composition was 57° C., and no crystallization could be observed. Observation was carried out down to −50° C., but no smectic phase other than $S_c^*$ phase appeared. The value of spontaneous polarization was 8 nC/cm$^2$ and the tilt angle was 29°.

In addition, a mixture having removed sample No. a21 of the present invention from the above composition, i.e. consisting only of the above three components each in equal weights exhibited the following complicated phase transitions:

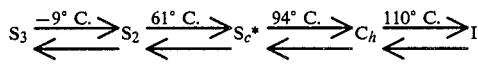

and the temperature range of $S_c^*$ phase was 61°–94° C.

As described above, the compounds of formula (I) are effective in spreading the temperature range of Sc* phase, particulary the lower range thereof.

EXAMPLE 6 (USE EXAMPLE 3)

Compounds of sample Nos. a16, a17, a11, a15 and a23 are blended at the respective ratios of 5%, 5%, 20%, 30% and 40% by weight to obtain a high dielectric liquid crystal composition having phase transition points of C-S$_c$*: 15° C., S$_c$*-SA 40.3° C., and SA-I: 46.3° C. at room temperature. Further, if this temperature range is insufficient, it is possible to make it more sufficient to meet an ordinal use by adding another liquid crystal having smectic C phase or chiral smectic C phase.

EXAMPLE 7 (USE EXAMPLE 4)

A nematic liquid crystal composition consisting of

was filled in a cell composed of transparent electrodes obtained by applying PVA as an agent for aligning treatment, followed by rubbing the resulting surface to subject it to a parallel aligning treatment, and having a distance between the electrodes, of 10 μm to prepare a TN type display cell, which was then observed under a polarizing microscope. As a result, a reverse twist domain was observed to be formed.

To the above nematic liquid composition was added a compound (sample No. a28 in Table 1) i.e.

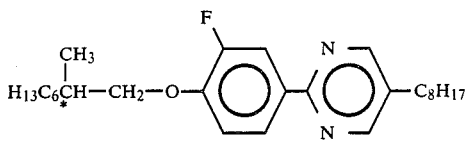

in 1% by weight, and the resulting composition was similarly observed in a TN type cell. As a result, the reverse twist domain was dissolved and a uniform nematic phase was observed.

What we claim is:

1. A liquid crystalline, halogen-containing heterocyclic compound expressed by the formula

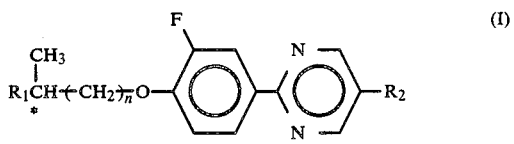

wherein R$_1$ represents C$_2$H$_5$ and R$_2$ represents an alkyl group of 6 to 12 carbon atoms; n represents an integer of 3 to 7; and the symbol * represents an asymmetric carbon atom.

2. A compound according to claim 1 wherein said compound is an optically active substance based on the asymmetric carbon atom in said formula (I).

3. A compound according to claim 1 wherein said compound is a racemate.

4. A chiral smectic C liquid crystal composition comprising at least two components at least one of which is a liquid crystalline, halogen-containing compound as set forth in claim 1.

5. A liquid crystal composition according to claim 4 wherein said compound is an optically active substance.

6. A liquid crystal composition according to claim 5, further containing a racemic, halogen-containing heterocyclic compound.

7. In a light switching element employing a chiral smectic C liquid crystal composition, the improvement wherein a composition according to claim 4 is employed.

8. A compound according to claim 1 wherein R$_1$ represents C$_2$H$_5$, R$_2$ is C$_8$H$_{17}$ and n is 5.

* * * * *